United States Patent [19]

Forester et al.

[11] Patent Number: 4,651,716
[45] Date of Patent: Mar. 24, 1987

[54] METHOD AND DEVICE FOR ENHANCEMENT OF CARDIAC CONTRACTILITY

[75] Inventors: George V. Forester, Ottawa; Alan J. Mortimer, Gloucester; Orest Z. Roy, Ottawa, all of Canada

[73] Assignee: Canadian Patents and Development Limited, Ottawa, Canada

[21] Appl. No.: 793,787

[22] Filed: Nov. 1, 1985

Related U.S. Application Data

[63] Continuation of Ser. No. 552,712, Nov. 17, 1983, abandoned.

[30] Foreign Application Priority Data

Dec. 3, 1982 [CA] Canada .................................. 416992

[51] Int. Cl.[4] ........................... A61N 5/00; A61B 6/00
[52] U.S. Cl. .................................. 128/1 D; 128/24 A; 128/660
[58] Field of Search .............. 128/1 D, 24 A, 419 D, 128/660

[56] References Cited

U.S. PATENT DOCUMENTS

| 3,735,756 | 5/1973 | Richards et al. | 128/24 A |
|---|---|---|---|
| 3,871,360 | 3/1975 | Van Horn et al. | 128/671 |
| 3,951,140 | 4/1976 | Eggleton et al. | 128/661 |
| 3,954,098 | 5/1976 | Dick et al. | 128/660 |
| 4,016,871 | 4/1977 | Schiff | 128/1 D |
| 4,094,310 | 6/1978 | McEachern et al. | 128/419 D |
| 4,204,524 | 5/1980 | Martin et al. | 238/1 D |
| 4,216,766 | 8/1980 | Duykers et al. | 128/24 A |
| 4,303,075 | 12/1981 | Heilman et al. | 128/419 D |
| 4,399,703 | 8/1983 | Matzuk | 128/660 |
| 4,462,402 | 7/1984 | Silverstein et al. | 128/660 |

FOREIGN PATENT DOCUMENTS

| 38080 | 10/1981 | European Pat. Off. | 128/419 D |
|---|---|---|---|
| 2400733 | 8/1974 | Fed. Rep. of Germany | 128/1 D |

OTHER PUBLICATIONS

Lehman, *Therapeutic Heat and Cold:* Third Edition ©1982, published by Williams & Wilkins, Baltimore/London, pp. 524–525.

Primary Examiner—William E. Kamm
Assistant Examiner—Mitchell J. Shein
Attorney, Agent, or Firm—Robert G. Hendry; Yoshiharu Toyooka

[57] ABSTRACT

An apparatus for ultrasonic irradiation of the heart either when the chest is open after surgery or through the chest wall. It may also be used in conjunction with electrical defibrillation equipment or alone. The apparatus includes an EKG for detecting the heart beat, an ultrasonic generator and timing and pulsing circuits for providing timed pulses of ultrasound to coincide with selected events in the cardiac cycle.

10 Claims, 8 Drawing Figures

METHOD AND DEVICE FOR ENHANCEMENT OF CARDIAC CONTRACTILITY

This is a continuation of application Ser. No. 552,712, filed Nov. 17, 1983, now abandoned.

This invention relates to producing an enhancement of cardiac contractility through the use of ultrasound.

More particularly, the present invention provides a method of improving cardiac performance by applying ultrasound to the heart itself, either internally from a catheter placed within the heart, by ultrasound irradiation applied on the surface of the body, or by ultrasound irradiation applied directly in contact with the heart. Ultrasound is also applied in combination with an electrical defibrillator or pacemaker. The invention also relates to a method for application of ultrasound for well defined and selectable periods of time arranged to coincide with critical events in the cardiac cycle.

In addition, the invention relates to a method for the application of ultrasound for well defined and selectable periods of time related to critical events in the process of electrical defibrillation.

When the ultrasound waves produced by the transducers are adjusted such that their energy traverses the heart itself, the action of the waves can exert their effect by creating microthermal heating, microcirculation changes, stirring, stable cavitation, microstreaming, or chemical effects. The differential heating is produced because of the known property of ultrasound to be absorbed by tissues according to their viscosities. Thus, organelle membranes within the heart absorb more energy than cytoplasmic components. It is thus expected that the sarcoplasmic reticulum being an internally located organelle within the heart would absorb energy and be heated preferentially before cytoplasm. Similarly, the sarcolemma and its internal projections—the transverse and longitudinal transverse system would also be heated more than extracellular areas and cytoplasm. Because of the differential heating, one would expect biologic activities associated with these membranous components to be stimulated.

Thus, we find a linear relationship between myocardial enhancement between 0.2 watt/$cm^2$ and 2.0 W/$cm^2$ SATA of ultrasound exposure. This implies that when energy from ultrasound is applied within a range to increase differential heating within the limits commensurate with biologic activity (<44° C.) we can selectively improve myocardial performance. Our experimental evidence shows that a portion of the ultrasound effect is produced via an increase of the efficiency of the excitation-contraction coupling system. Secondly, the action potential of ultrasound irradiated cells indicates an improvement in calcium transfer across the membrane in the plateau phase. Both of these facts suggest that ultrasound modifies sarcolemmal (external muscle membrane) characteristics. The ultrasound effects are completely reversible as opposed to conventional drug therapies.

The changes in the action potential characteristics are consistent with the view that membrane properties and, hence, biologic properties are temporarily modified by ultrasound. Such changes would alter the sodium-potassium ATPase. This is seen in the resting nonexcited heart muscle as a rapid hyperpolarisation of the membrane potential which can be interpreted as an increase in the activity of the $Na^+$-$K^+$ATPase of sarcolemma. Secondly, the rapid increase in the overshoot of the cardiac 'action potential' with ultrasound points to an alteration in membrane permeability with ultrasound during membrane excitability. Caffeine at 2.5-3.5 mM/L will block the ultrasound effect showing that the sarcoplasmic reticulum is an integral part of the expression of the ultrasound enhancement. With caffeine and hypernatremia, we obtain an increase in diastolic tension rather than a decrease. This also shows that the sarcoplasmic reticulum is implicated in the expression of the ultrasound effect. The ultrasonic production of myocardial enhancement can be produced through a number of modes. It is most rapid with continuous wave ultrasound but it may also be produced with improved efficiency but at a slight loss in rapidity with pulsed ultrasound. Thus ultrasound pulsed in conjunction with an EKG signal through an appropriate circuit can also limit whole heart heating but produce the differential heating in the most advantageous portion of the cardiac cycle to enhance the contractile behaviour of the heart. Pulsed, continuous wave, or a combination of both, may be used in an predetermined or spontaneous mode to irradiate the heart according to the clinical condition of the patient.

Mode of Application

Application in closed chest mode (extrathoraic application):

In such a case as where a patient exhibits cardiac failure and has a ventricular tachycardia or ventricular fibrillation, ultrasound may be applied by using in the first instance, a transducer aimed at the heart and placed between the 4th and 5th ribs to the region of the heart. The transducer is held firmly in place against the chest and transmission is aided within a suitable coupling mechanism. The ultrasound irradiation is either applied continuously or timed to the EKG signal via the coupling circuit. In this way, ultrasound reaching the heart can effect the changes described in this application.

In the case of a fibrillating heart, the ultrasound may be applied through a transducer as above, prior to defibrillation or may be applied as an integral part of the defibrillating electronics as described in this application. The application of ultrasound preceding the defibrillation charge is usually as a continuous wave. However, the control circuit will apply ultrasound in a pulsed mode as soon as an EKG signal is generated. Thus the ultrasound may be applied before, during and after the defibrillation in order to enhance the recovery of the myocardium.

In the case where a pacemaker is used to program a heart beat cycle and inserted temporarily or permanently into a patient, the extrathoraic application of ultrasound may be used to augment the performance of a weakened heart. Preferably, ultrasound pulses are timed to coincide with a selected event in the programmed beat cycle.

Open Chest Application:

Where the heart of a patient is exposed due to a surgical intervention, such as in open heart surgery, the ultrasound may be applied by a transducer or transducers directly to the heart with a suitable coupling medium. This would be especially useful following open heart surgery where the circulation of the blood and perfusion of the body has been performed by mechanical means and must be transferred to the heart itself. The heart being in a weakened condition from the period of anoxia and trauma, it cannot immediately perform the work necessary to sustain the circulation and may ultimately fail. The use of ultrasound to augment cardiac performance will result in a quicker and more sustained recovery from the intra-operative state.

In the case where the heart will not resume its beat with or without pacing and reverts to random electrical and mechanical activity (fibrillation) or tachycardia, the use of ultrasound with or without the defibrillatory shocks, as shown in this application, will induce rhythmical electrical and mechanical activity, decreasing the time to recover from this potentially catastrophic event(s).

In the case where a patient's heart can be weaned successfully from a mechanical pumping device (heart-lung machine), the application of ultrasound directly to the heart as described in this invention will assist in the recovery phase of the immediate post-operative condition.

In the case where ultrasound would have to be applied by a miniature transducer to the heart, inserted via a catheter to the left or right myocardium in a vein or artery, the ultrasound probe may be inserted quickly if a patient in a critical state requires cardiac enhancement, such as in case of shock, low volume syndrome (hemorrhage), nervous system damage, brain damage or malfunction, myocardial ischemia, or angina attacks. This may be applied in hospital or in an emergency vehicle, or in the field. Furthermore, the device can be used as a tool in the study of the functioning of the heart as an investigative instrument.

Ultrasound must be applied to the heart in order to effect an improvement in the cardiac performance. The present invention provides methods of applying ultrasound having a frequency greater than 20 KHz and up to 25 MHz during critical periods of the cardiac cycle, without damage to intervening tissue or the heart itself in order to improve cardiac contractility.

Accordingly, the present invention provides an apparatus for ultrasonic enhancement of cardiac contractility, said apparatus comprising means for detecting a heart beat, means for generating ultrasound, and means for providing timed pulses of said ultrasonic energy, each said pulse to coincide with a selected event in the cardiac cycle.

DETAILED DESCRIPTION

Figure 1:
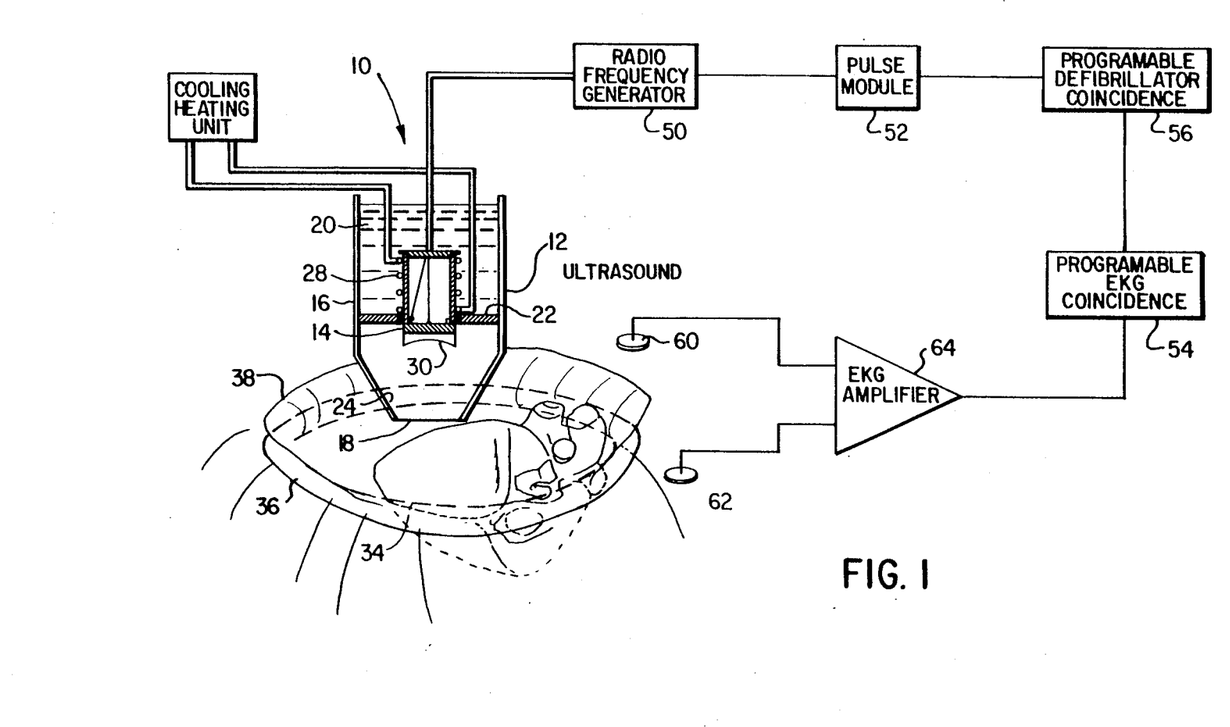
FIG. 1 is a diagrammatic illustration of the ultrasonic cardiac contractility enhancing apparatus of this invention as it would appear in use during heart surgery.

Referring now in detail to the drawings, the ultrasonic cardiac enhancer apparatus shown generally at 10 in FIG. 1, for use in intraoperative application, includes a transducer assembly, shown at 12. The ultrasound is produced by a piezoelectric material or other means 14 mounted in a housing 16 of suitable plastic material. The front face of the housing 16 has a membrane or cover 18 of material, such as latex rubber or mylar, to provide maximum transmission of ultrasound to the degassed water coupling medium 20 surrounding the transducer 12. The transducer 12 is centered in the transducer housing 16 by means of a transducer centering device 22 so that the ultrasound energy exits from the transducer housing 16 in an unimpeded manner. The ultrasound leaves the transducer housing 16 through an acoustic window 24 which provides very little disruption in the ultrasound beam. To maintain the transducer housing 16 and, particularly portions of the transducer housing 16 in contact with the patient at body temperature, heating/cooling coils 28 are placed in the water coupling mechanism surrounding the transducer.

Figure 2:
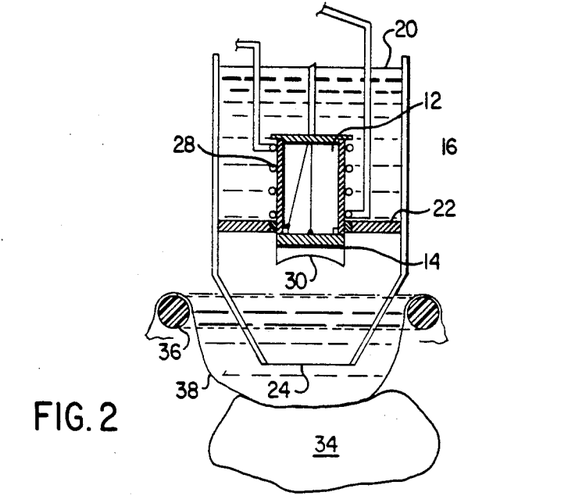
FIG. 2 is a sectional side elevational view of the ultrasonic transducer of FIG. 1.

The ultrasound irradiator used for closed chest application of ultrasound contains all the features described previously. In addition, a focussing element 30 of acrylic or other suitable material, is placed in front of the transducer 12 to focus the ultrasound to a point within the water bath coupling medium adjacent to the acoustic window 24. This feature provides a narrow beam to pass through small spaces between bones yet the beam expands to irradiate a large portion of the heart. In practice, the acoustic window 24 in the transducer housing 16 must be in physical contact with the heart 34 or the abdomen (not shown), respectively, in order that ultrasound may be transmitted. The ultrasonic transducer device 10, FIGS. 1 and 2, is coupled to the myocardium in such a way that the transducer does not exert pressure on the heart so as to impede its free movement. This is achieved by placing a silastic covered ring 36 around the thoracic opening to the myocardium and using the ring to support a sac 38 of polyvinylidene chloride film which is filled with sterile degassed water. The film is approximated to the surface of the heart and adheres to the surface assuming the shape of the myocardium as the myocardium moves. Physical contact to the heart is maintained by a coating of sterile acoustic coupling gel. The transducer assembly is then lowered into the water sac and suspended above the film-heart surface but below the water surface, this effectively allows the ultrasound waves to pass from the transducer to the myocardium freely.

Figure 3:
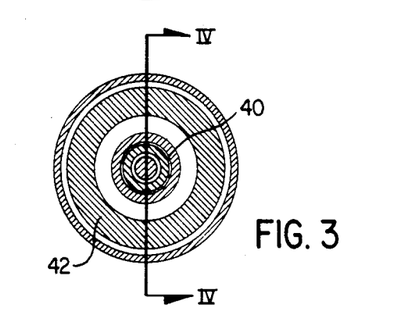
FIG. 3 is a bottom plan view of an ultrasonic transducer combined with an electric defibrillator.
Figure 4:
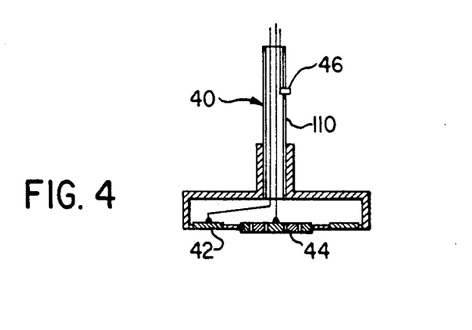
FIG. 4 is a cross-sectional side elevational view of the transducer of FIG. 3 taken along the line 4—4 of FIG. 3.

The irradiator for applications in defibrillation is shown generally at 40 in FIGS. 3 and 4. The irradiator 40 consists of two main elements, an annular electrode 42 used to apply the electrical energy required for defibrillation, and an ultrasound transducer 44 consisting of several concentric rings of piezoelectric or other material, to produce ultrasound energy which may be directed into the body at an angle dependent on the relative size of the concentric rings 44. The ultrasound and electrical energy is initiated by a pushbutton 46 attached to the irradiator 40 which is connected to the programmable defibrillator circuit, to be described below.

In practice, the ultrasound transducer defibrillator paddle 40 is applied to the chest in the region of an intercostal space overlying the heart, physical contact with the thorax is made by the use of an acoustically and electrically conductive gel or a saline solution. The return defibrillator electrode of conventional design (not shown) is placed as in conventional practice. The type of fibrillation to be treated is selected from the console and the button on the handle pushed to activate the device. Further, the same instrument may be used for defibrillation in an inoperative setting with lower electrical energy applied.

The system shown in FIG. 1 includes one of the ultrasound transducers described above, a radio frequency electrical generator 50 which is activated by a pulse module 52 controlled to produce pulses allowing ultrasound from continuous wave to 3 sec pulses by a programmable electrocardiograph (EKG) coincidence circuit 54, and a programmable defibrillator coincidence circuit 56.

Figure 5:
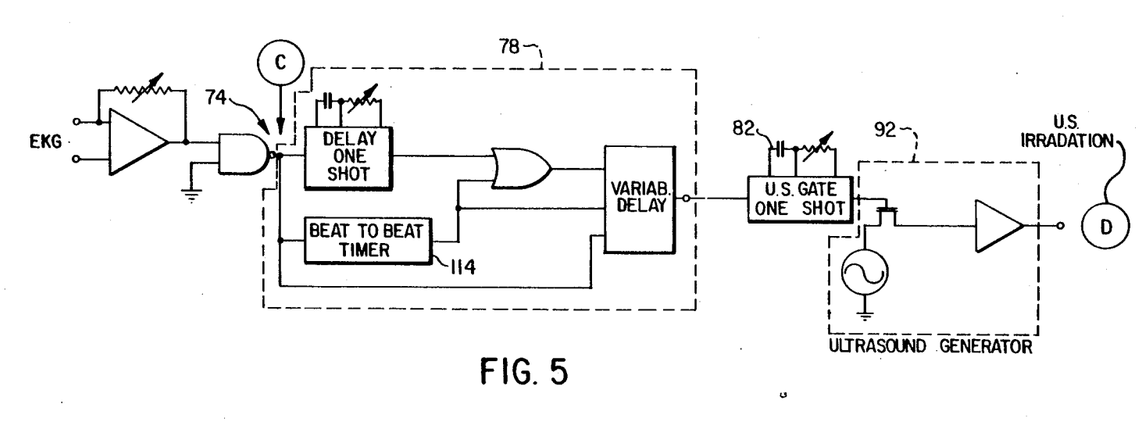
FIG. 5 is a schematic drawing of the electrical control circuit of the embodiment of FIGS. 1 and 2.
Figure 7:
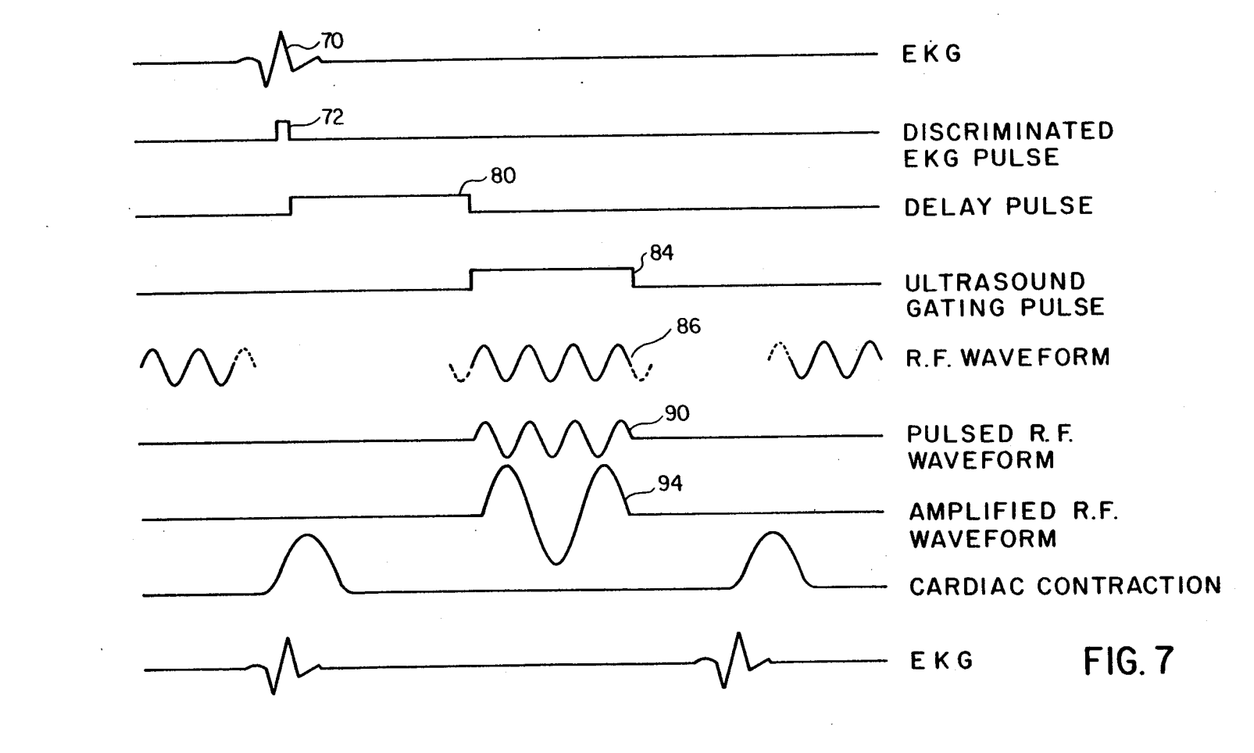
FIG. 7 is an illustration of the signal forms at different points in the circuitry of FIG. 5.

A pulse of ultrasonic energy of variable duration and intensity related to critical events in the cardiac cycle may be produced as shown in FIG. 7. The EKG signal is acquired by conventional EKG electrodes 60 and 62 and amplified by a high gain amplifier 64 to produce the EKG signal 70, shown in FIG. 7. The EKG signal 70 is shaped in a timing start pulse 72 by a discriminator circuit, shown generally at 74 in FIG. 5. The discriminator circuit 74 activates a delay circuit 78, as shown in FIG. 5, which provides the appropriate delay interval 80 (FIG. 7) and may be adjusted automatically or externally to compensate for heart rate and critical events within the heart pertaining to the condition which is being treated. The delay interval generating circuit triggers an ultrasound gating pulse circuit 82 which produces a ultrasound gating pulse 84 of adjustable width from 3 sec to infinite length. The ultrasound gating pulse 84 is applied to radio frequency (r.f.) wave 86 in the pulse module circuit to generate a pulsed radio frequency waveform 90. This pulsed r.f. waveform 90 is amplified by the generator circuit 92 and the amplified waveform 94 is applied to an ultrasonic transducer to produce a pulse of ultrasonic energy at appropriate times with respect to the cardiac cycle.

FIG. 7 further includes a graph showing the cardiac contractions in the cardiac cycles. The graph indicates the ventricular pressure in relation to the EKG signals as customarily done in the medical field. The cardiac contraction is called systole and the relaxation following each systole is called diastole. As seen from FIG. 7, a pulse of ultrasound which in coincident with the pulse of amplified RF waveform is applied during a period of a diastole and, accordingly, is of a duration shorter than the period of each diastole. As also illustrated in FIG. 7, the ultrasound generating means in response to each ultrasound gating pulse generates a pulse of ultrasound having a duration substantially the same as that of the ultrasound gating pulse. As further illustrated in FIG. 7, in the processing of an EKG signal, the signal is discriminated to provide a discriminated EKG pulse which produces a delayed pulse leading to the ultrasound gating pulse.

Figure 6:
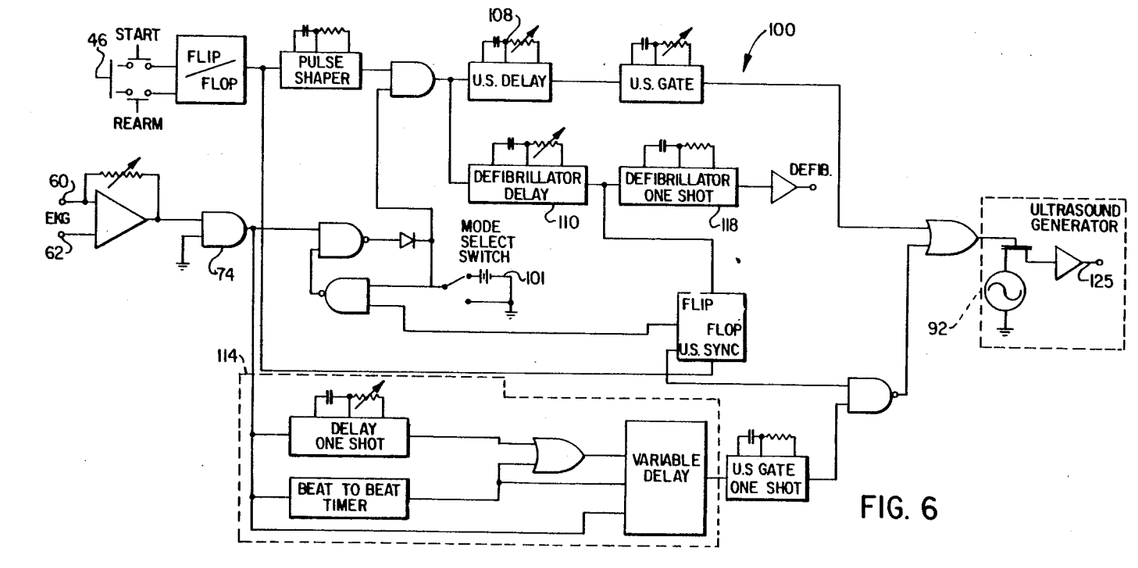
FIG. 6 is a schematic drawing of the control circuit for the embodiment of FIGS. 3 and 4.

Further to the above circuits, a programmable defibrillator circuit (shown at 100 in FIG. 6) may be used for ultrasonic treatment to improve recovery from defibrillation. Electrical defibrillation may be applied in the absence of EKG as occurs with ventricular fibrillation or synchronized to the EKG for inversion of atrial fibrillation by use of a mode switch 101. In either case, once the heart is beating, the ultrasoud may be applied at critical intervals within the cardiac cycle as described previously. The circuits described allow ultrasound to be applied for predetermined and accurately controlled times with respect to the defibrillation pulse or accurately applied with respect to the contraction of the heart and the electrical defibrillation pulse, in order to improve cardiac performance.

Figure 8:
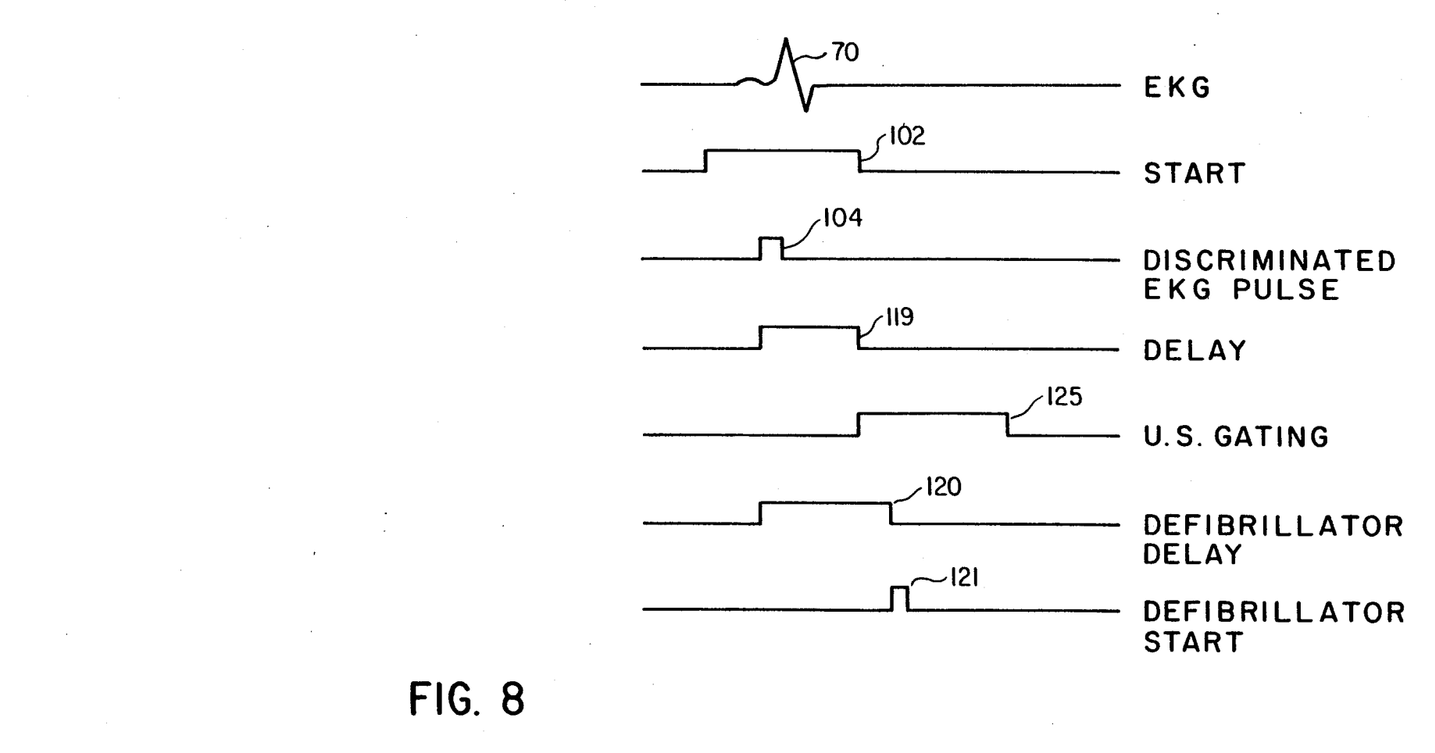
FIG. 8 is an illustration of the signal forms at different points in the circuitry of FIG. 6.

The operational sequence shown in FIG. 8 is initiated by a short pulse 102 from the pushbutton switch 46 (FIG. 6) on the defibrillator 40. If EKG synchronization has been selected, the EKG signal 70, from patient electrodes 60 and 62, is formed into the discriminated EKG pulse 104. The EKG pulse 104 in turn activates two delay circuits 108 and 110, the ultrasound timing circuit 114, and the defibrillator timing circuit 118 (shown in FIG. 6). The lengths of these two delays 119 and 120 specify the order of occurrence of defibrillation and ultrasound irradiation. In most cases of ventricular fibrillation, applition of ultrasound is initiated prior to defibrillation, whereas in some cases of atrial fibrillation, the two events need to be closely synchronized as described previously. The defibrillator delay pulse 120 actuates a defibrillator start circuit 118, which sends a defibrillator start pulse 121 to a defibrillator unit. The ultrasound delay 108 activates an ultrasound gating circuit, the output of which (125) is applied to the synchronized ultrasound generating circuits described previously to produce ultrasound energy which is applied to the heart.

In six experiments on cat hearts, in situ, under conditions of increased pacing rate, an increase in ventricular blood pressure and aortic blood flow of 10% was noted when ultrasound was applied during the critical portion of the cardiac cycle, timed with respect to the EKG. If the ultrasound was applied without appropriate delay, a depression in both parameters of approximately 4% was noted. The increase observed increased with ultrasonic intensity. In the experiments an increase in the ventricular pressure of the heart (20 mm Hg) was noticed when pulsed ultrasound was applied.

When the cardiovascular system of the cat was depressed by an increased pacing rate, synchronized pulsed ultrasound was observed to lead to a more rapid recovery than under control conditions, without ultrasound. In experiments on 15 cats, recovery occurred within three minutes compared to recovery times exceeding five minutes without pulsed ultrasound.

We claim:
1. A method of ultrasound enhancement of the cardiac contractility of a patient's heart under treatment comprising the steps of
continuously acquiring EKG signals reperesenting actual cardiac cycles of the heart, each cycle consisting of a systole and a diastole,
discirminating each of the EKG signals to generate a discriminated EKG pulse,
generating in response to each of the EKG pulses a delay pulse indicative of a delay interval,
producing an ultrasound gating pulse in response to each of the delay pulses, the said ultrasound gating pulse having a duration shorter than the period of each diastole,
activating ultrasound generating means in response to each of the untrasound gating pulses to generate a pulse of ultrasound having a duration the same as that of the ultrasound gating pulse and the intensity of between 0.2 W/cm$^2$ and 2.0 W/cm$^2$ SATA, and
applying the said pulses of ultrasound to the heart under treatment in such a manner that each of said pulses of ultrasound is applied during the period of each diastole so that the contractility of the heart is enhanced.

2. The method according to claim 1 wherein the step of activating the said ultrasound generating means comprises the steps of generating RF waveforms to drive the said ultrasound generating means, and gating the said RF waveforms in response to each of the ultrasound gating pulses to operate the said ultrasound generating means to generate a pulse of ultrasound having a duration the same as that of the ultrasound gating pulse.

3. The method according to claim 1 wherein the delay interval and the duration of the ultrasound gating pulse are adjustable with respect to the EKG pulse so that each of the said pulses of ultrasound is applied adjustably in time and duration during the period of each diastole.

4. The method according to claim 1 wherein the said pulses of ultrasound are applied to the heart externally of the patient's chest through adjacent ribs.

5. The method according to claim 1 wherein the ultrasound generating means generate pulses of ultrasound whose frequency is within the range of about 20 KHz to about 25 MHz.

6. An apparatus for ultrasonic enhancement of the cardiac contractility of a patient's heart under treatment comprising EKG means for continuously acquiring EKG signals representing actual cardiac caycles of the heart, each cycle consisting of a systole and a diastole, discriminating means for discriminating each of the EKG signals to generate a discriminated EKG pulse, delay means for generating in response to each of the EKG pulses, a delay pulse indicative of a delay interval, gating pulse means for producing an ultrasound gating pulse in response to each of the delay pulses, the said ultrasound gating pulse having a duration shorter than the period of each diastole, activating means, including ultrasound generating means for generating, in response to each of the ultrasound gating pulses, a pulse of ultrasound having a duration the same as that of the ultrasound gating pulse and the intensity of between 0.2 W/cm$^2$ and 2.0 W/cm$^2$ SATA, and application means for applying the said pulses of ultrasound to the heart under treatment so that each of said pulses of ultrasound is applied during the period of each diastole.

7. The apparatus according to claim 6 wherein the activating means comprises the ultrasound generating means operative with RF waveforms, RF generating means for generating RF waveforms, and gate means for gating the RF waveforms in response to each of the ultrasound gating pulses to operate the said ultrasound generating means to generate a pulse of ultrasound having a duration the same as that of the ultrasound gating pulse.

8. The apparatus according to claim 6 wherein the delay interval and the duration of the ultrasound gating pulse are adjustable with respect to the EKG pulse so that each of the said pulses of ultrasound is applied adjustably in time and duration during the period of each diastole.

9. The apparatus according to claim 6 wherein the activating means further comprise a focusing element provided on the said ultrasound generating means to direct the said pulses of ultrasound to pass between adjacent ribs in the patient's chest and to diverge to contact a greater area of the heart.

10. The apparatus according to claim 6 wherein the ultrasound generating means generates ultrasound of a frequency within the range of about 20 KHz to about 25 MHz.

* * * * *